United States Patent [19]

Perras

[11] 4,359,908
[45] Nov. 23, 1982

[54] ELECTRICAL BUSHING GAS SAMPLING APPARATUS AND METHOD

[75] Inventor: Arnold M. Perras, Dalton, Mass.
[73] Assignee: General Electric Company
[21] Appl. No.: 221,014
[22] Filed: Dec. 29, 1980
[51] Int. Cl.³ .............................................. G01N 1/10
[52] U.S. Cl. ............................. 73/863.85; 174/11 BH
[58] Field of Search .................... 174/11 BH, 11 R; 73/863.85

[56] References Cited

U.S. PATENT DOCUMENTS

| | | | |
|---|---|---|---|
| 2,279,230 | 4/1942 | Frost | 174/11 BH |
| 3,238,784 | 3/1966 | Dorsey et al. | 73/863.85 |
| 3,550,452 | 12/1970 | Halasz et al. | |
| 3,693,455 | 9/1972 | Harding et al. | 73/864.86 |
| 3,767,835 | 10/1973 | Englehardt | 174/11 BH |
| 3,776,042 | 12/1973 | Werra et al. | |
| 4,273,951 | 6/1981 | Terreri | 174/11 BH |

FOREIGN PATENT DOCUMENTS 87640  7/1956  Norway .......................... 73/863.85

Primary Examiner—S. Clement Swisher
Attorney, Agent, or Firm—Robert A. Cahill

[57] ABSTRACT

A sealable membrane is inserted within the filler plug receptacle of a high voltage bushing for providing access to the gas space above the dielectric oil used within the bushing. Gas sampling is achieved by inserting the needle of a hypodermic syringe through the membrane and withdrawing a quantity of gas to be sampled. The sealable properties of the membrane allow a plurality of samples to be taken without destroying the gas-tight seal.

10 Claims, 3 Drawing Figures

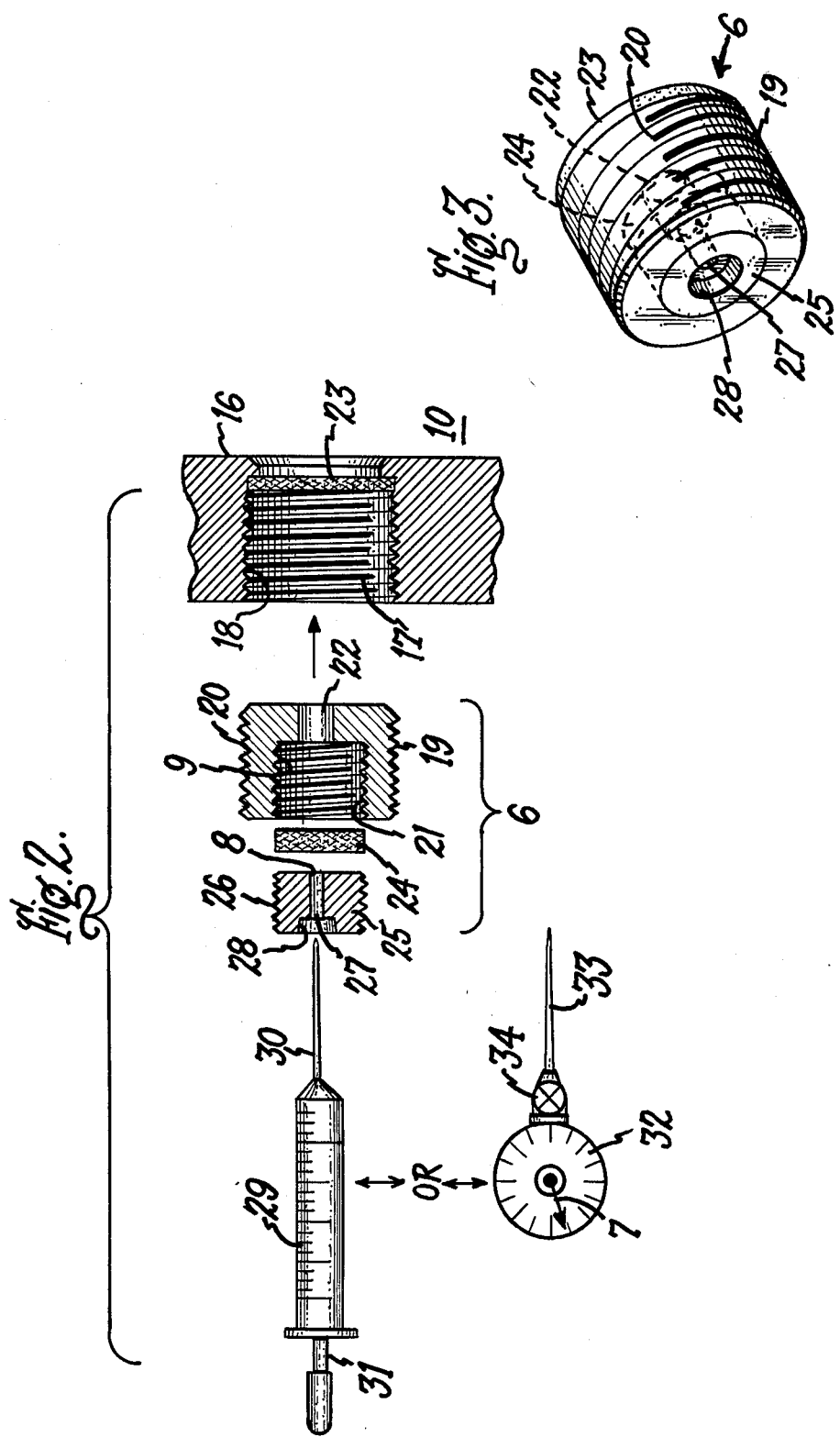

ELECTRICAL BUSHING GAS SAMPLING APPARATUS AND METHOD

BACKGROUND OF THE INVENTION

High voltage bushings used within power transformers generally contain a quantity of dielectric oil for cooling and insulating the bushing electrodes. Over long periods of operation, the gas space above the surface of the oil dielectric can become contaminated by the gaseous byproducts of the decomposition of the insulation material used within the bushing. A sampling of the gaseous material in the space above the oil dielectric can therefore give an indication as to the condition of the oil dielectric and the paper dielectric materials within the bushing for incipient fault detection. Current means for sampling the gaseous materials existing above the oil dielectric generally involve surrounding the top portion of the bushing oil fill hole plug with an airtight enclosure and evacuating, then introducing the gaseous material to within the enclosure. There is often the question as to whether the atmosphere within the enclosure dilutes or otherwise affects the measured pressure and composition of the gaseous materials being tested.

The purpose of this invention is to describe methods and apparatus for rapidly and reliably obtaining samples of the gaseous materials existing above the oil dielectric in electrical bushings without the requirement for auxiliary housings or similar airtight enclosures.

SUMMARY OF THE INVENTION

The invention comprises an adapter for connecting with a high voltage electrical bushing to allow a gas sample to be withdrawn from the expansion space above the oil dielectric within the bushing. The adapter includes a sealable membrane connected to the bushing by means of a passage plug member. A hypodermic syringe is inserted through the passage and penetrates the sealable membrane without introducing any external gaseous or atmospheric materials to the bushing. A further embodiment includes a gauge member which can be removably inserted through the membrane for direct reading of the gas pressure within the bushing.

BRIEF DESCRIPTION OF THE DRAWINGS

FIG. 2 is a side view of the bushing of FIG. 1 including the gas-sampling apparatus according to the invention; and FIG. 3 is a side perspective view of the assembled apparatus depicted in FIG. 1.

DESCRIPTION OF THE PREFERRED EMBODIMENT

Figure 1:
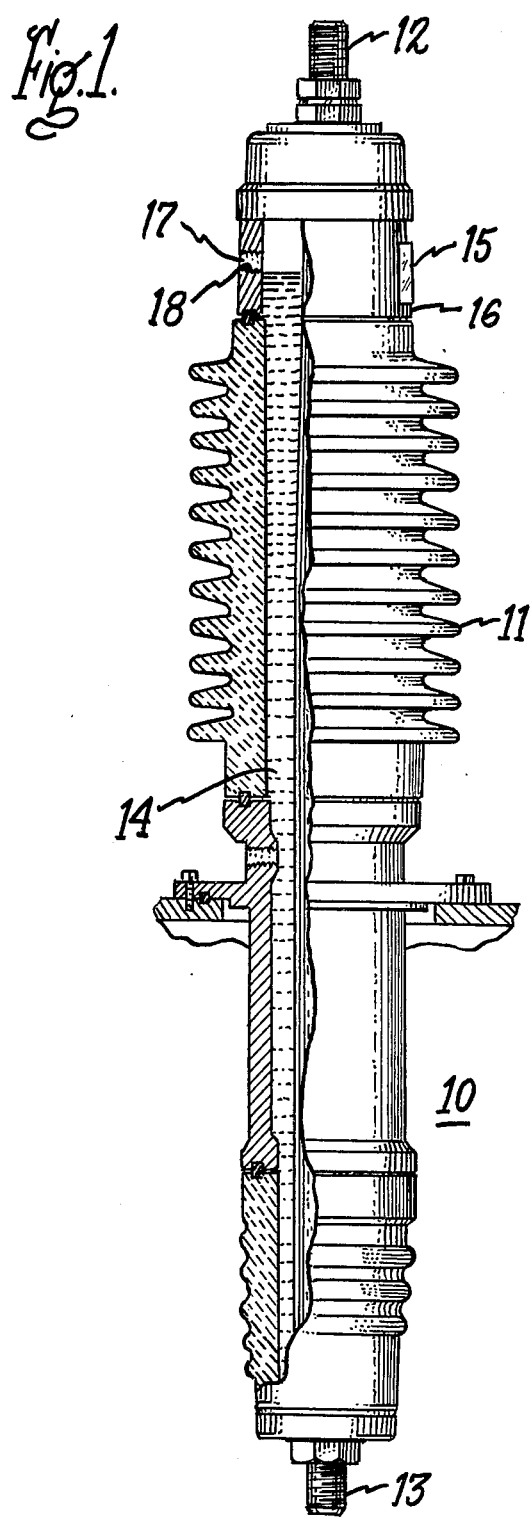
FIG. 1 is a front perspective view, in partial section, of an electrical bushing used with the method and apparatus of the instant invention.

FIG. 1 shows an electrical bushing 10 of the type including a porcelain skirt section 11 and a top and bottom electrode, 12, 13, which are internally electrically connected. In order to insulate and cool the bushing a quantity of oil dielectric 14 is included within the major interior portion of the bushing. To determine the level of oil dielectric 14 a sight glass 15 is provided within the metal section 16 which supports top electrode 12. To provide for the filling and draining of oil dielectric 14 a passage 17 is included within metal section 16 and includes internal thread 18 for insertion of a pipe plug.

FIG. 3 shows a portion of bushing 10 including a sealable membrane 23 which functions to provide a gas-tight seal between passage 17 and the interior of bushing 10. Membrane 23 replaces the usual O ring member that is employed with the pipe plug described earlier. Membrane 23 is formed from a material such as silicon, rubber or plastic which can "heal" itself after being penetrated by a sharp object such as a hypodermic needle. A first plug 19 having a plurality of external threads 20 for engaging with internal thread 18 on bushing 10 and having formed therein internal threads 21 is employed for holding membrane 23 in place. A passage 22 in the form of a concentric hole is provided within plug 19 to provide access to membrane 23. In one embodiment of the instant invention, bushing 10 is provided with membrane 23 and plug 19 is threadedly inserted within passage 17 to provide an airtight closure. When samples are required to be taken of the gaseous materials above the oil dielectric 14, shown in FIG. 1, a hypodermic syringe 29 is inserted within passage 22 by means of a hollow needle 30 having a side port 5 which prevents needle clogging and membrane tearing to penetrate membrane 23. Plunger 31 is then slowly retracted to withdraw a quantity of the gaseous material within hypodermic syringe 29. The gaseous sample can then be brought to a gas analyzer, such as a gas chromatograph, for analysis. To facilitate fastening plug 19 within passage 17, a portion of passage 22 can comprise a hex-like configuration to accommodate an Allen wrench. A second membrane 24 can be inserted within groove 9 provided within plug 19 in order to further seal passage 22 from the atmosphere. Membrane 24 is held in place by a second plug 25 containing external threads 26 for engaging with internal threads 31 within groove 9. Second plug 25 includes a passage 8 and a tapered guide hole 27 for facilitating and guiding the passage of needle 30. Passage 8 being slightly larger than syringe needle 30 prevents unguided penetrations and tatterings of membranes 23, 24 and thereby promotes longer membrane life. With second plug 25 and membrane 24 in place within plug 19 and plug 19 in place within slot 17, needle 30 is inserted within passage 8 through membrane 24, through passage 22 and through membrane 23 to obtain the gas sample. Membrane 24 is made of a material similar to that for membrane 23 and has similar sealable properties. One of the main reasons for the use of membrane 24 is to determine whether membrane 23 remains gastight over many applications. Needle 30 can be inserted through membrane 24 without penetrating membrane 23 to sample the atmosphere existing in the close vicinity of membrane 23. If gaseous contaminants are found external to membrane 23 and internal to the area intermediate membrane 24 and membrane 23, then membrane 23 should be replaced or a new membrane 24 will then be relied upon for sealing. The provision of tapered slot 27 within second plug 25 is to facilitate the entrance of needle 30 within passage 8 without damaging needle 30. In the event that second plug 25 and membrane 24 are not employed, passage 22 can have a tapered slot similar to slot 27 to facilitate the entrance of needle 30 directly to within passage 22. In order to determine the pressure of the gaseous contaminants or the nitrogen blanket, which is oftentimes employed, a gauge 32 can be employed in the following manner. Gauge 32 is first evacuated by connecting needle 33 to a vacuum system and opening valve 34 to cause indicator 7 to come to a reference zero. Valve 34 is then closed and needle 33 is removed from the vacuum system. Needle 33 is then inserted in a manner similar to that described earlier for operation of hypodermic syringe 29, and valve 34 is opened in order to obtain a pressure reading on 32 of the gaseous material existing within bushing 10. The movement of indicator 7 then provides a measure of the gas pressure within bushing 10 and, if readings are taken over extended periods of time, can provide an indication as to whether the nitrogen blanket within bushing 10 is leaking to the atmosphere or whether the dielectric materials are deteriorating. Besides using hypodermic syringe 29 to remove a small sample of the gaseous material within bushing 10, it can also be used to supply nitrogen gas to bushing 10 in the following manner. Hypodermic syringe needle 30 and 30A assembly are connected with a nitrogen supply hose with pipe fittings. The nitrogen gas can then be introduced into bushing 10 by the insertion of needle 30 in the manner described earlier.

The interconnection between plugs 25, 19 and membranes 24, 23 is shown at 6 in FIG. 3. The complete unit 6 can be installed at the time of manufacture of bushing 10 or in the field as a replacement for the oil fill plug described earlier or offered as an option for bushings made prior to the invention.

What is claimed as new and which it is desired to secure by Letters Patent of the United States is:

1. An adapter for providing gas sampling facility to an electrical bushing comprising:
    a first sealable membrane seated in the fill plug receptacle of an electrical bushing for providing a gas-tight seal to said bushing;
    a first plug member having external threads for threaded engagement in the fill plug receptacle to retain said first membrane therein and an internally threaded bore terminating in a reduced diameter central passage;
    a second sealable membrane seated in said threaded bore of said first plug member; and
    a second plug member having external threads for threaded engagement in said threaded bore of said first plug member to retain said second membrane therein and a central passage aligned with said central passage of said first plug member to accommodate the insertion of a syringe needle through said first and second membranes.

2. The adapter of claim 1 wherein said passage of said first plug member includes a hex-shaped cross section portion for receiving an Allen wrench.

3. The adapter of claim 1 wherein said passage within said plug member includes a tapered opening at one end to assist in guiding the entrance of the syringe needle.

4. The adapter of claim 3 wherein said passage of said second plug member includes a portion having a hex configuration for accepting an Allen wrench.

5. An electrical bushing comprising:
    a pair of first and second electrodes separated by means of a porcelain-skirted body section for providing electrical insulation between said first and second electrodes;
    an oil-fill plug receptacle within said bushing;
    a sealable membrane within said receptacle for providing a gastight seal to said bushing; and
    a plug member having a passage therethrough for insertion within said receptacle to retain said membrane within said receptacle.

6. The bushing of claim 5 further including a groove within said plug member for retaining a second sealable membrane for providing a further gas-tight seal to said receptacle.

7. The bushing of claim 6 further including a second plug member having a passage for insertion within said first plug groove for retaining said second membrane within said groove.

8. The bushing of claim 7 wherein said plug member and said second plug member both contain a slot having a hex configuration for accommodating an Allen wrench.

9. The bushing of claim 7 wherein said second plug member includes a tapered slot for facilitating the insertion of a hypodermic needle for removing samples of gas contaminants from said bushing.

10. A method for adapting an electrical bushing to provide gas sampling facility comprising the steps of:
    inserting a sealable membrane within an oil-fill inlet within an electrical bushing; and
    inserting at least one plug having a passage extending through the cross section of said plug for retaining said membrane within said inlet, said passage defining means for receiving a hypodermic needle.

* * * * *